(12) United States Patent
Chiang et al.

(10) Patent No.: US 9,889,036 B2
(45) Date of Patent: Feb. 13, 2018

(54) JOINT ORTHOSIS

(71) Applicant: Plus Meditech Co., Ltd., Tainan (TW)

(72) Inventors: Yueh-Hua Chiang, Taipei (TW); Fu-Lin Chuang, Tainan (TW); Chien-Min Fang, Tainan (TW)

(73) Assignee: Plus Meditech Co., Ltd., Tainan (TW)

( * ) Notice: Subject to any disclaimer, the term of this patent is extended or adjusted under 35 U.S.C. 154(b) by 540 days.

(21) Appl. No.: 14/674,577

(22) Filed: Mar. 31, 2015

(65) Prior Publication Data

US 2016/0058596 A1    Mar. 3, 2016

(30) Foreign Application Priority Data

Aug. 27, 2014 (TW) .............................. 103129546 A

(51) Int. Cl.
*A61F 5/01* (2006.01)

(52) U.S. Cl.
CPC .... *A61F 5/0123* (2013.01); *A61F 2005/0139* (2013.01); *A61F 2005/0158* (2013.01); *A61F 2005/0165* (2013.01); *A61F 2005/0172* (2013.01); *A61F 2005/0179* (2013.01)

(58) Field of Classification Search
CPC .................. A61F 5/0123; A61F 5/0125; A61F 2005/0132–2005/0179; Y10T 403/17; Y10T 403/59; Y10T 403/591; Y10T 403/599; Y10T 403/60; Y10T 403/602; Y10T 403/604; Y10T 403/606
See application file for complete search history.

(56) References Cited

U.S. PATENT DOCUMENTS

| | | | |
|---|---|---|---|
| 7,887,496 B2* | 2/2011 | Kahlmeyer | A61F 5/0123 16/221 |
| 8,920,349 B2* | 12/2014 | Ferrigolo | A61F 5/0123 602/16 |

\* cited by examiner

*Primary Examiner* — Victoria J Hicks
*Assistant Examiner* — Michelle J Lee
(74) *Attorney, Agent, or Firm* — Hamre, Schumann, Mueller & Larson, P.C.

(57) ABSTRACT

A joint orthosis includes upper and lower members, and a joint mechanism. The joint mechanism includes a shielding cover and at least one of modular front and rear inserts. Each of the modular front and rear inserts is disposed to limit movement of a joint of a human body in a flexion/extension direction. The shielding cover is removably attached to a mounting frame of the joint mechanism and is configured to conceal and prevent access to the at least one or the modular front and rear inserts.

10 Claims, 11 Drawing Sheets

JOINT ORTHOSIS

CROSS-REFERENCE TO RELATED APPLICATION

This application claims priority from Taiwanese application no. 10312956, filed on Aug. 27, 2014, the disclosure of which is incorporated in its entirety herein by reference.

FIELD OF THE INVENTION

This invention relates to a joint orthosis, more particularly to a joint orthosis with modular front and rear inserts that are less likely to fall out.

BACKGROUND OF THE INVENTION

A joint orthosis can be used to support and stabilize a human joint, especially a torn anterior cruciate ligament in a knee joint. The joint orthosis can be used for limiting movement of the torn anterior cruciate ligament in extension and flexion directions.

U.S. Pat. No. 7,887,496 discloses a joint orthosis which includes an upper member, a lower member operably connected to the upper member by one or more swivel axes at a joint mechanism, and a pad attached to the joint mechanism and positioned between the joint mechanism and a body part. In order to limit flexion of the knee joint, a stop insert may be inserted between two discs of the joint mechanism. On at least one side of the stop insert, a key element, in the form of an elevation, locks into a corresponding recess in the two discs to prevent the stop insert from falling out. The stop insert can be easily grabbed, and pulled out of the joint mechanism via a nub thereof, to adjust the flexion angle limits.

However, wear of the elevation of the stop insert over time might result in falling out of the stop insert from the joint mechanism.

SUMMARY OF THE INVENTION

Therefore, an object of the present invention is to provide a novel joint orthosis having a shield cover to prevent modular front and rear inserts from falling out.

Accordingly, a joint orthosis of the present invention includes upper and lower members, at least one of modular front and rear inserts, a mounting frame, a pad bracket, upper and lower pivot bolts, and a shielding cover. The upper member includes an upper pivot segment which has an upper pivot bore defining an upper axis and an upper peripheral interacting region that extends angularly about the upper axis and that includes a front upper terminal area, a rear upper terminal area, and upper teeth that are displaced from each other about the upper axis and that are disposed between the front and rear upper terminal areas. The lower member includes a lower pivot segment which has a lower pivot bore defining a lower axis and a lower peripheral interacting region that extends angularly about the lower axis and that includes a front lower terminal area, a rear lower terminal area, and lower teeth that are displaced from each other about the lower axis, and that are disposed between the front and rear lower terminal areas. The front upper and lower terminal areas cooperatively define therebetween a front contoured area having a first front dimension. The rear upper and lower terminal areas cooperatively define therebetween a rear contoured area having a first rear dimension. The upper and lower teeth interlock with each other such that when at least one of the upper and lower members is permitted to rotate about at least a corresponding one of the upper and lower axes, the front and rear contoured areas are transformed from having the first front and rear dimensions to having second front and rear dimensions, respectively. The modular front and rear inserts each are configured to be fitted in a corresponding one of the front and rear contoured areas having the second front and rear dimensions, respectively, and each have an inner major surface, an outer major surface, and a protuberance extending outwardly from the enter major surface. The mounting frame is disposed outwardly of the upper and lower pivot segments, and has front and rear jaw cavities each of which is configured to permit the respective protuberance to be engaged therein. The mounting frame further has upper and loser frame holes aligned with the upper and lower pivot bores, respectively. The pad bracket is disposed inwardly of the upper and lower pivot segments, and has an outward major surface confronting the upper and lower pivot segments, and an inward major surface adapted to be pressed against a pad. The pad bracket further has upper and lower bracket holes aligned with the upper and lower pivot bores, respectively. The upper pivot bolt is configured to pass through the upper frame hole, the upper pivot bore, and the upper bracket hole so as to permit the upper member to foe pivotally mounted thereon, thereby permitting the upper member to be pivotable about the upper axis relative to the mounting frame and the pad bracket. The lower pivot bolt is configured to pass through the lower frame hole, the lower pivot bore, and the lower bracket hole so as to permit the lower member to be pivotally mounted thereon, thereby permitting the lower member to be pivotable about the lower axis relative to the mounting frame and the pad bracket. The shielding cover is removably attached to the mounting frame, and is configured to conceal and prevent access to the at least one of the modular front and rear inserts.

BRIEF DESCRIPTION OF THE DRAWINGS

Other features and advantages of the present invention will become apparent in the following detailed description of the embodiment of the invention, with reference to the accompanying drawings, in which.

DETAILED DESCRIPTION OF THE EMBODIMENT

Figure 1:
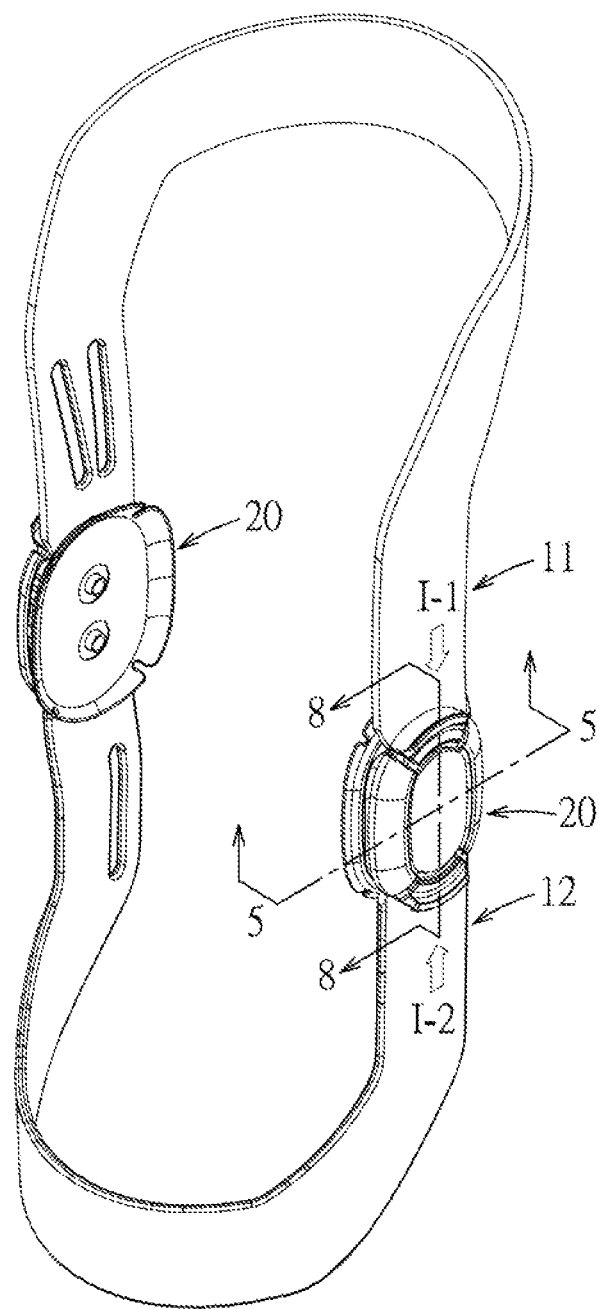
FIG. 1 is a perspective view of a joint orthosis according to an embodiment of the present invention.

FIG. 1 shows a joint orthosis according to an embodiment of the present invention. In this embodiment, the joint orthosis includes upper and lower members 11, 12, and two joint mechanisms 20. Alternatively, the joint orthosis may include a single joint mechanism 20.

Figure 2:
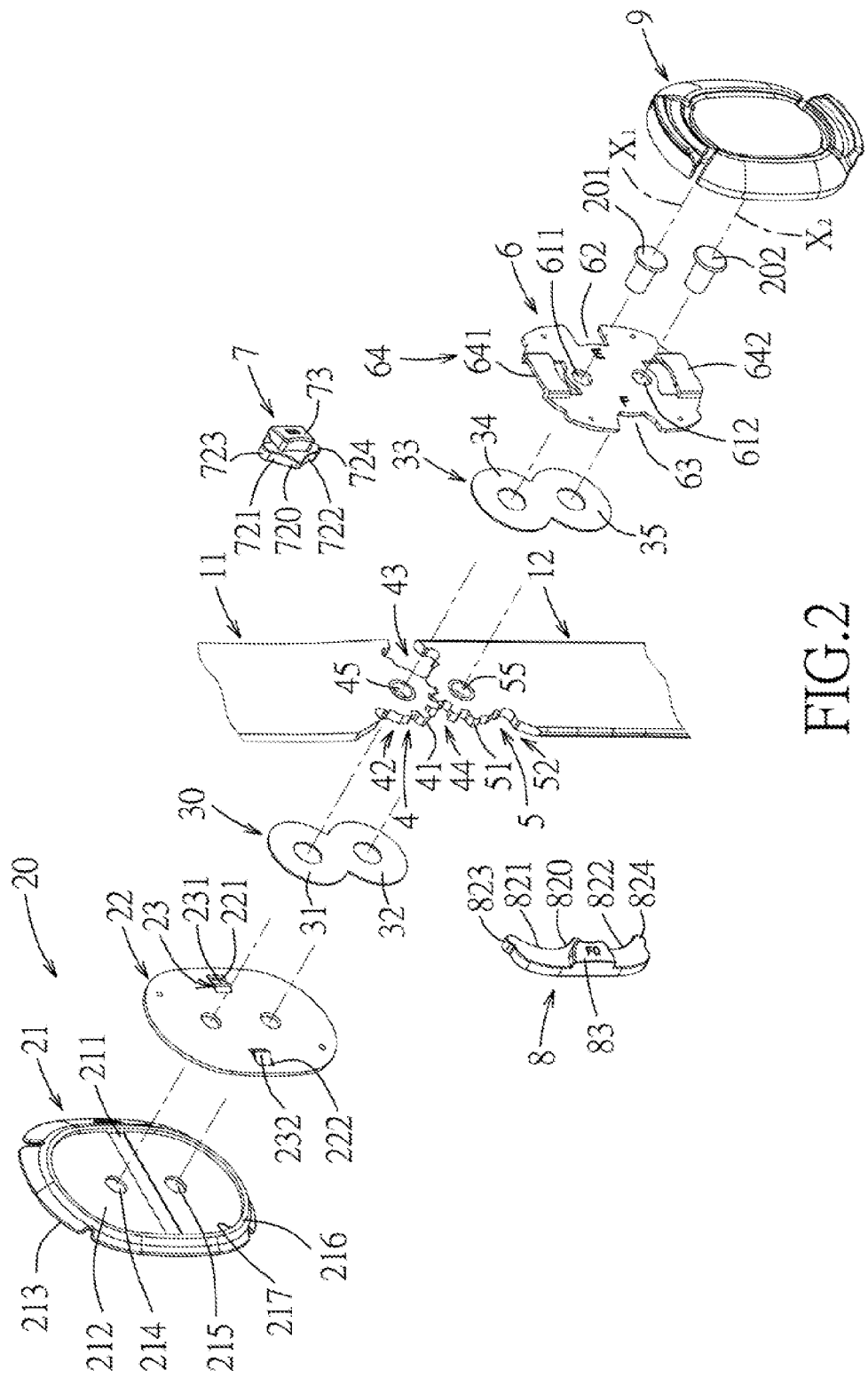
FIG. 2 is a fragmentary exploded perspective view of the joint orthosis.
Figure 6:
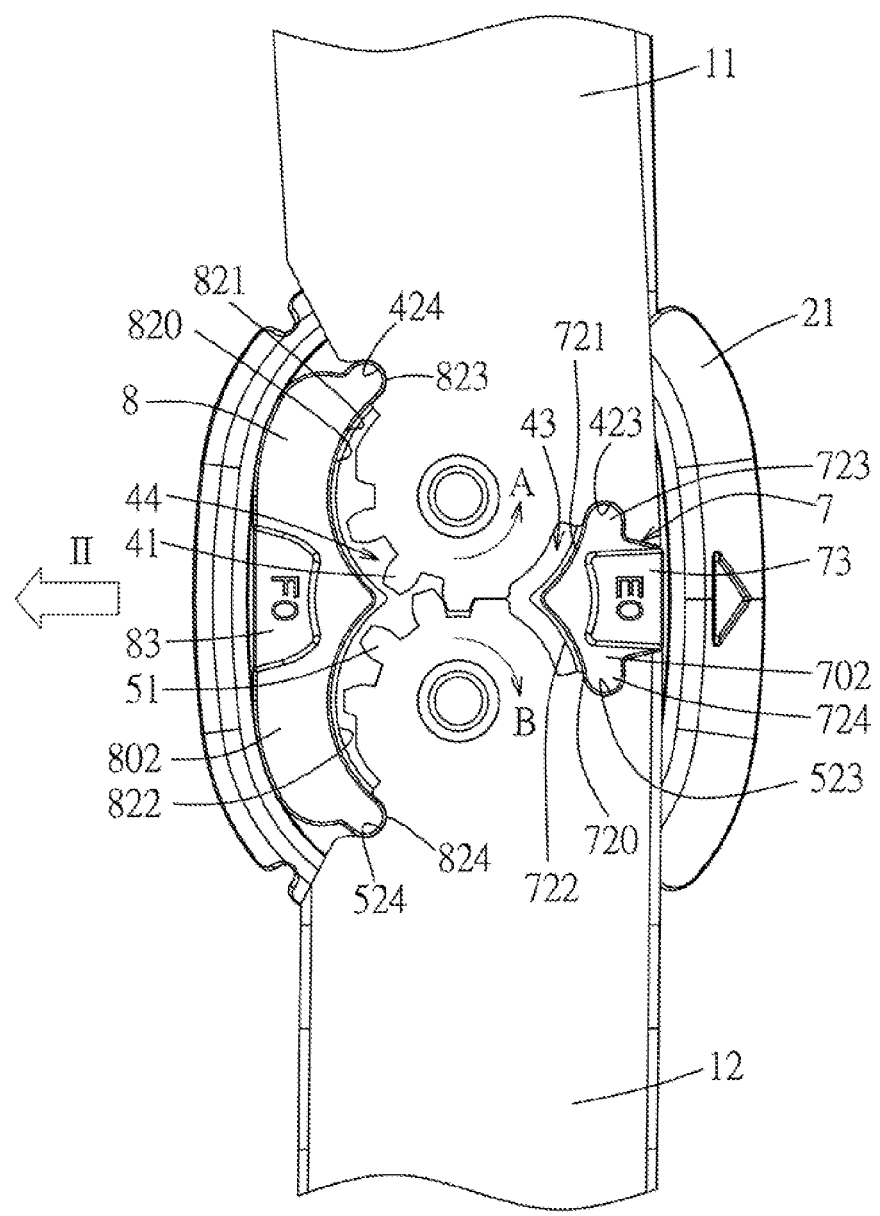
FIG. 6 is a fragmentary enlarged view of the joint orthosis.
Figure 12:
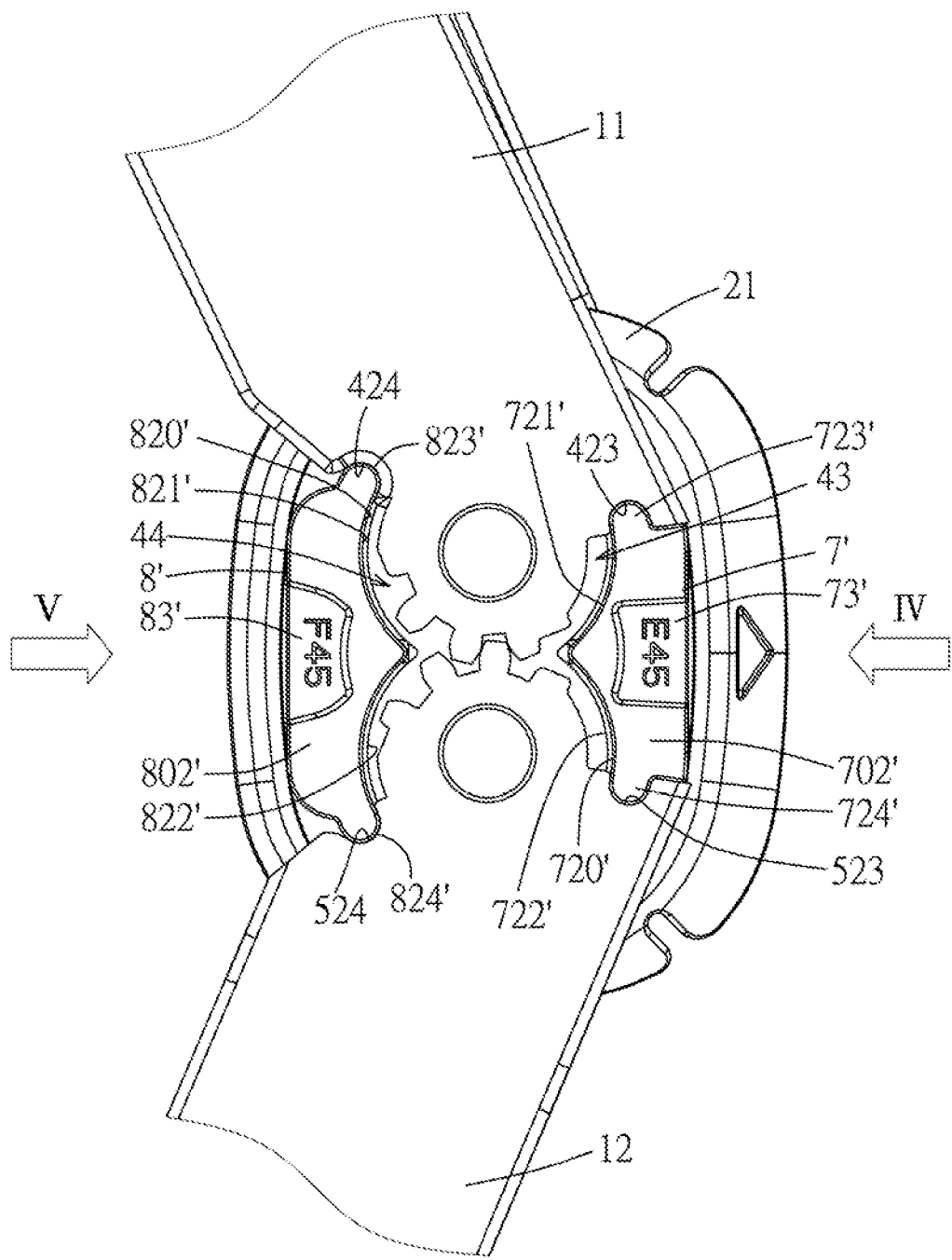
FIG. 12 is a fragmentary enlarged view similar to FIG. 6 but illustrating that the joint orthosis is fitted with two other inserts.

As shown in FIGS. 2, 6, and 12, each joint mechanism 20 includes at least one of modular front and rear inserts 8, 8', 7, 7', a mounting frame 6, a pad bracket 21, upper and lower pivot bolts 201, 202, and a shielding cover 9.

The upper and lower members 11, 12 are curved splints made from a light weight material. Examples of the light weight material may include, but are not limited to, aluminum, aluminum alloys, carbon fibers, carbon steel, copper alloys, magnesium alloys, titanium, titanium alloys, etc.

Figure 4:
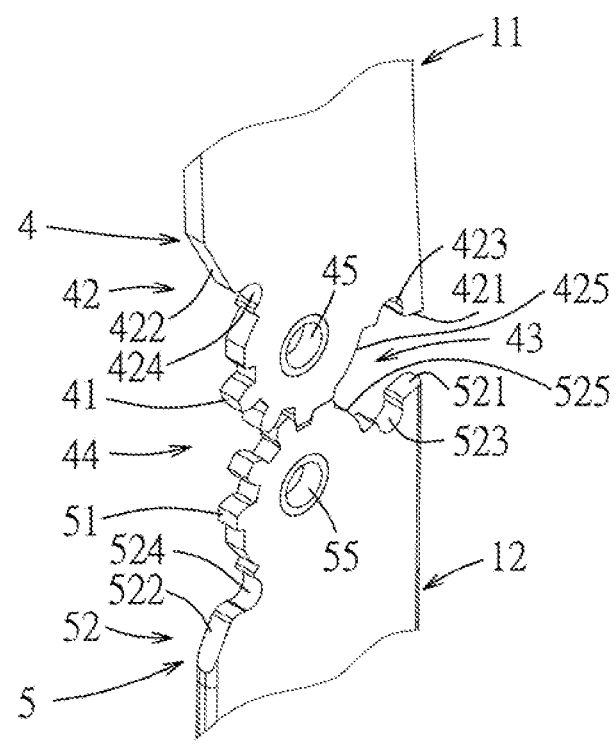
FIG. 4 is a fragmentary enlarged view of upper and lower members shown in FIG. 2.

As shown in FIGS. 2 and 4, the upper member 11 includes an upper pivot segment 4 which has an upper pivot bore 45 defining an upper axis ($X_1$) and an upper peripheral interacting region 42 that extends angularly about the upper axis ($X_1$) and that includes a front upper terminal area 422, a rear upper terminal area 421, and upper teeth 41 (see FIG. 4). The upper teeth 41 are displaced from each other about the upper axis ($X_1$) and are disposed between the front and rear upper terminal areas 422, 421. The front upper terminal area 422 is formed with a front upper mortise cavity 424, and the rear upper terminal area 421 is formed with a rear upper mortise cavity 423. The upper peripheral interacting region 42 further includes an upper toothless area 425 disposed between the rear upper terminal area 421 and the upper teeth 41.

The lower member 12 includes a lower pivot segment 5 which has a lower pivot bore 55 defining a lower axis ($X_2$) and a lower peripheral interacting region 52 that extends angularly about the lower axis ($X_2$) and that includes a front lower terminal area 522, a rear lower terminal area 521, and lower teeth 51 (see FIG. 4). The lower teeth 51 are displaced from each other about the lower axis ($X_2$), and are disposed between the front and rear lower terminal areas 522, 521. The front lower terminal area 522 is formed with a front lower mortise cavity 524, and the rear lower terminal area 521 is formed with a rear lower mortise cavity 523. The lower peripheral interacting region 52 further includes a lower toothless area 525 disposed between the rear lower terminal area 521 and the lower teeth 51.

As shown in FIG. 4, the front upper and lower terminal areas 422, 522 cooperatively define therebetween a front contoured area 44 having a first front dimension. The rear upper and lower terminal areas 411, 521 cooperatively define therebetween a rear contoured area 43 having a first rear dimension. The upper and lower teeth 41, 51 interlock with each other such that when at least one of the upper and lower members 11, 12 is permitted to rotate about at least a corresponding one of the upper and lower axes ($X_1$, $X_2$), the front and rear contoured areas 44, 43 are transformed from having the first front and rear dimensions (FIG. 6) to having second front and rear dimensions (FIG. 12), respectively. The front and rear contoured areas 44, 43 may be further transformed from having the second front and rear dimensions to having the first front and rear dimensions.

Each of the modular front and rear inserts 8, 8', 7 or 7' is configured to be fitted in a corresponding one of the front and rear contoured areas 44, 43 when the front and rear contoured areas 44, 43 are transformed into the second front and rear dimensions, respectively.

In this embodiment, the joint orthosis includes a pair of the modular front inserts 8, 8' and a pair of the modular rear inserts 7, 7'. When the front and rear contoured areas 44, 43 have the first front and rear dimensions, respectively (FIG. 6), the modular front and rear inserts 8, 7 are fitted in the front and rear contoured areas 44, 43, respectively. When the front and rear contoured areas 44, 43 are transformed to have the second front and rear dimensions, respectively (FIG. 12), the modular front and rear inserts 8', 7' are fitted in the front and rear contoured areas 44, 43, respectively.

In other words, each of the front pair and the rear pair of the modular inserts 8, 8' or 7, 7' are configured to have different dimensions so as to respectively match the first and second dimensions of a corresponding one of the front and rear contoured areas 44, 43, respectively.

Figure 5:
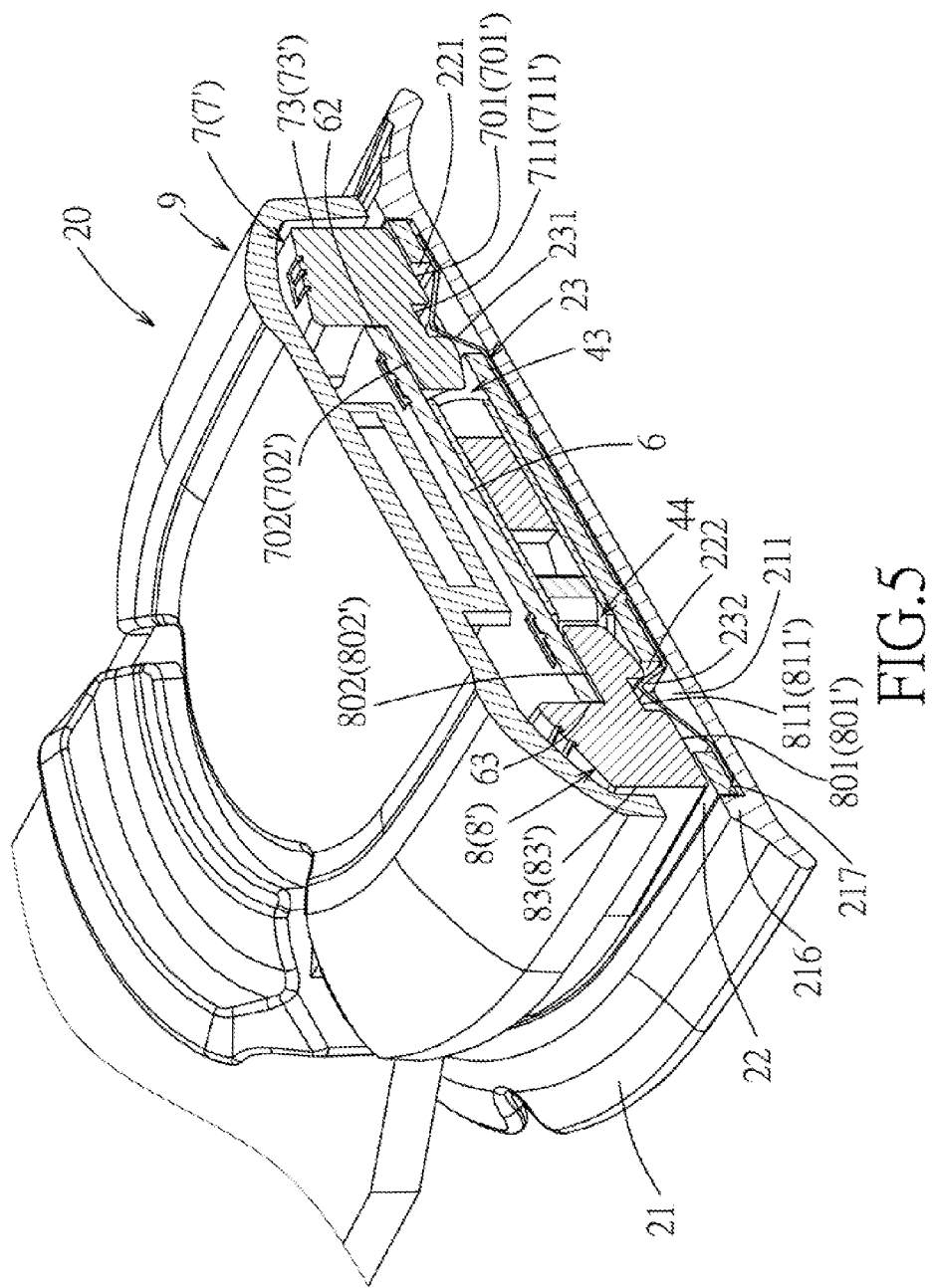
FIG. 5 is an enlarged cross-sectional view taken along line 5-5 of FIG. 1.

As best shown in FIGS. 5, 6 and 12, each modular front insert 8 or 8' has an inner major surface 801 or 801', an outer major surface 802 or 802', a protuberance 83 or 83', and a minor surface 820 or 820'. The protuberance 83 or 83' extends outwardly from the outer major surface 802 or 802'. The minor surface 820 or 820' includes upper and lower gliding regions 821, 822 or 821', 822' which extend respectively away from the protuberance 83 or 83' so as to permit the upper and lower teeth 41, 51 to freely glide thereon, and which extend to respectively terminate at upper and lower tenon ends 823, 824 or 823', 824'. When the modular front insert 8 or 8' is fitted in the front contoured area 44, the upper tenon end 823 or 823' is fitted in the front upper mortise cavity 424, and the lower tenon end 824 or 824' is fitted in the front lower mortise cavity 524 (see FIGS. 6 and 12).

Figure 8:
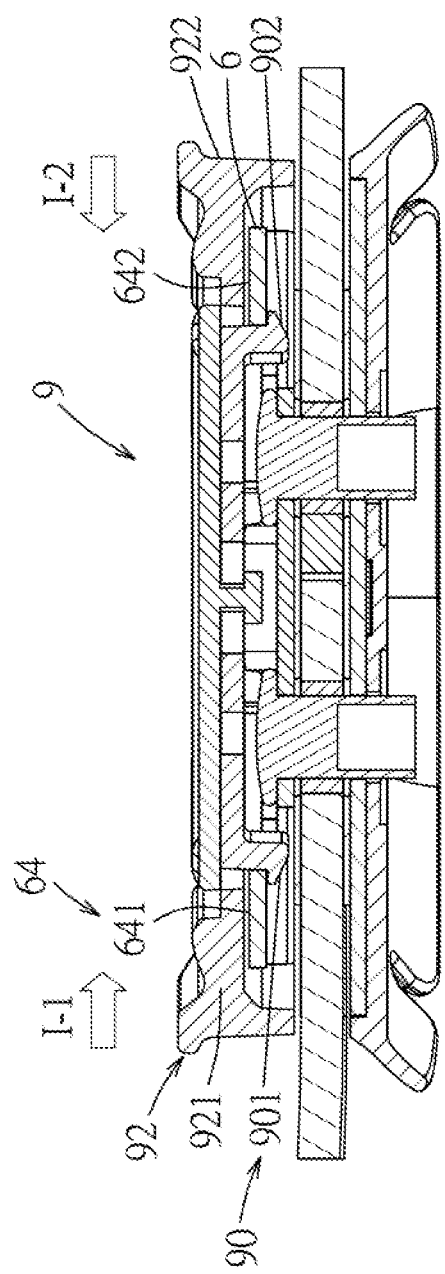
FIG. 8 is a cross-sectional view taken along line 8-8 of FIG. 1.

As best shown in FIGS. 5, 8 and 12, each modular rear insert 7 or 7' has an inner major surface 701 or 701', an outer major surface 702 or 702', a protuberance 73 or 73', and a minor surface 720 or 720'. The protuberance 73 or 73' extends outwardly from the outer major surface 702 or 792'. The minor surface 720 or 720' includes upper and lower gliding regions 721, 722 or 721', 722' which extend respectively away from the protuberance 73 or 73' so as to permit the upper and lower teeth 41, 51 to freely glide thereon, and which extend to respectively terminate at upper and lower tenon ends 723, 724 or 723', 724'. When the modular rear insert 8 or 8' is fitted in the rear contoured area 43, the upper tenon end 723 or 723' is fitted in the rear upper mortise cavity 423, and the lower tenon end 724 or 724' is fitted in the rear lower mortise cavity 523.

As shown in FIG. 2, the mounting frame 6 is disposed outwardly of the upper and lower pivot segments 4, 5, and has front and rear jaw cavities 63, 62. The front jaw cavity 63 is configured to permit the protuberance 83 or 83' of the modular front insert 8 or 8' to be engaged therein (see FIG. 5). The rear jaw cavity 62 is configured to permit the protuberance 73 or 73' of the modular rear insert 7 or 7' to be engaged therein. The mounting frame 6 further has upper and lower frame holes 611, 612 aligned with the upper and lower pivot bores 45, 55, respectively.

Figure 3:
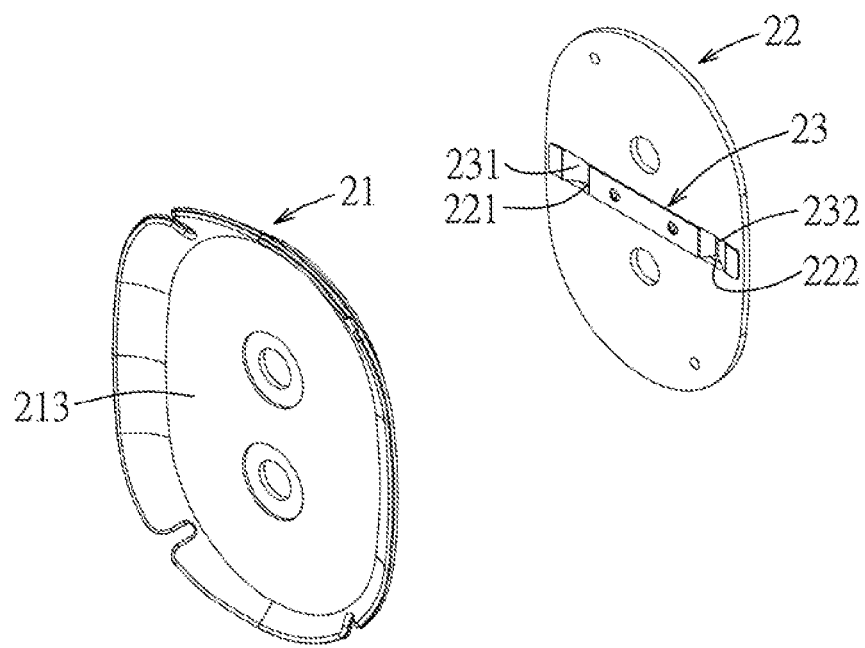
FIG. 3 is a perspective view of a pad bracket and a positioning plate of the joint orthosis of FIG. 2 taken from another angle.

As shown in FIGS. 2 and 3, the pad bracket 21 is disposed inwardly of the upper and lower pivot segments 4, 5, and has an outward major surface 212 confronting the upper and lower pivot segments 4, 5, and an inward major surface 213 adapted to be pressed against a pad (not shown). The pad bracket 21 further has upper and lower bracket holes 214, 215 aligned with the upper and lower pivot bores 45, 55, respectively.

The upper pivot bolt 201 is configured to pass through the upper frame hole 611, the upper pivot bore 45, and the upper bracket hole 214 so as to permit the upper member 11 to be pivotally mounted thereon, thereby permitting the upper member 11 to be pivotable about the upper axis ($X_1$) relative to the mounting frame 6 and the pad bracket 21.

The lower pivot bolt 202 is configured to pass through the lower frame hole 612, the lower pivot bore 55, and the lower bracket hole 215 so as to permit the lower member 12 to be pivotally mounted thereon, thereby permitting the lower member 12 to be pivotable about the lower axis ($X_2$) relative to the mounting frame 6 and the pad bracket 21.

The shielding cover 9 is removably attached to the mounting frame 6, and is configured to conceal and prevent access to at least one of the modular front and rear inserts 8, 8', 7, 7'.

Figure 7:
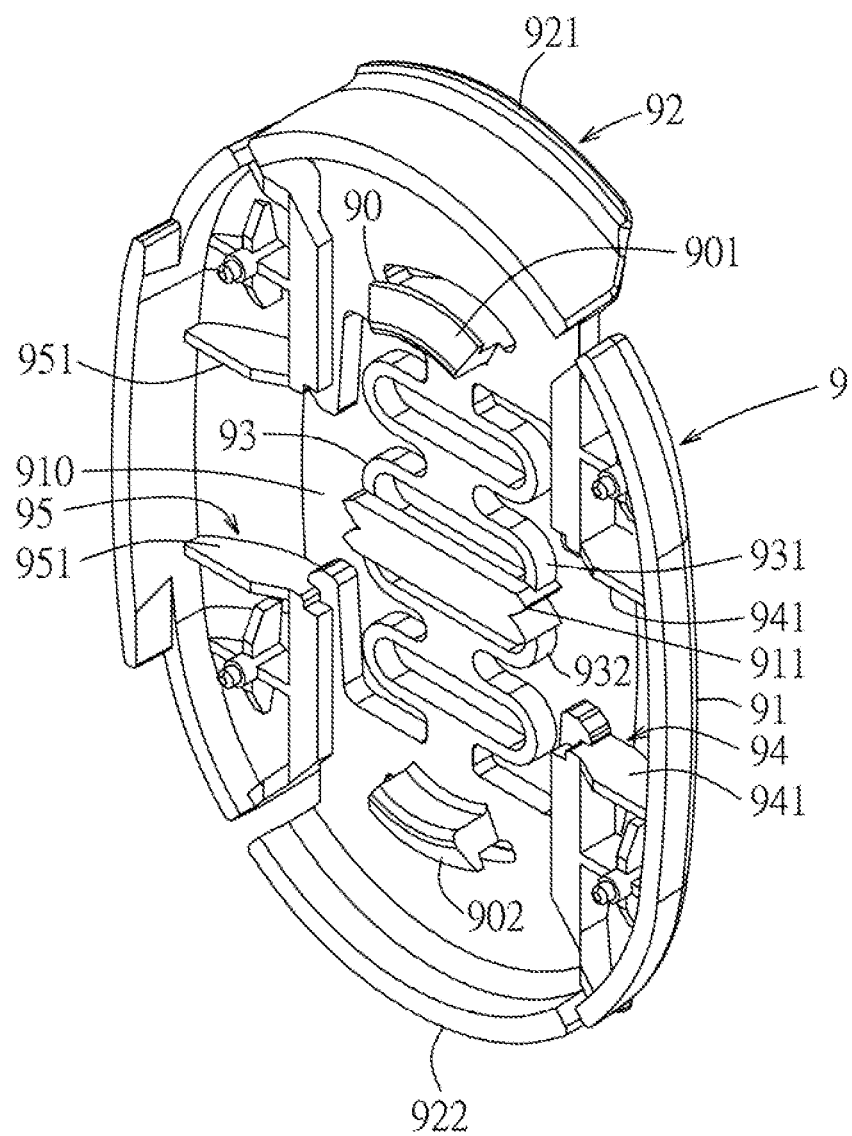
FIG. 7 is an enlarged perspective view of a shielding cover of the joint orthosis.

In this embodiment, the mounting frame 6 further has a retaining unit 64 (see FIG. 2), and the shielding cover 9 has a cover body 91, a latch pin unit 90, a press button unit 92, and a biasing unit 93 (see FIG. 7). The latch pin unit 90 is movable between an engaging position (FIG. 8), where the latch pin unit 90 is engaged with the retaining unit 64, and a disengaging position (FIG. 9), where the latch pin unit 90 is disengaged from the retaining unit 64. The biasing unit 93 is disposed to bias the latch pin unit 90 to the engaging position. The press button unit 92 is configured to be manually pressed against a biasing action of the biasing unit 93 to move the latch pin unit 90 to the disengaging position.

Figure 9:
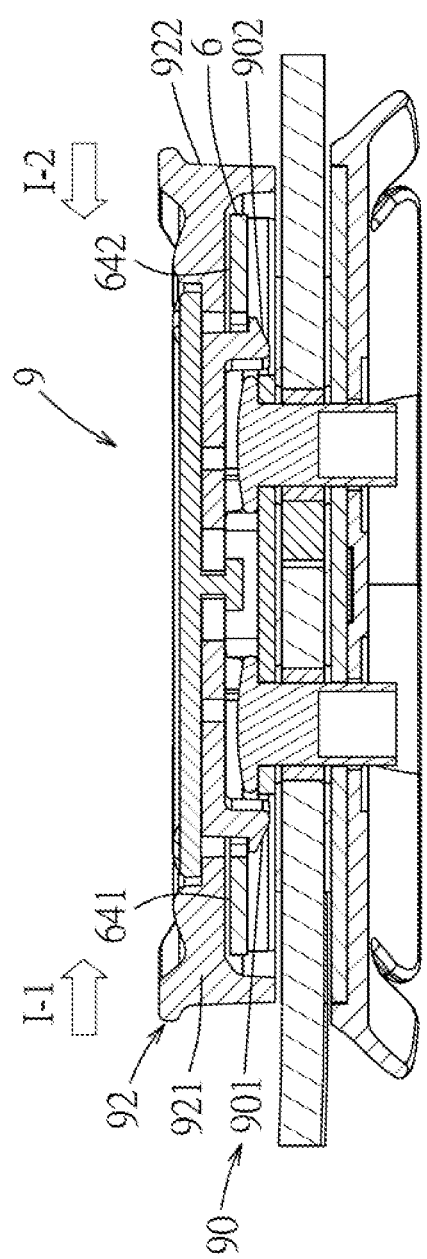
FIG. 9 is a cross-sectional view similar to FIG. 8 but illustrating that a latch pin unit of the shield cover is disengaged from a retaining unit of a mounting frame.

The retaining unit 64 includes upper and lower retaining members 641, 642 (see FIGS. 2, 8, and 9). The press button unit 92 includes upper and lower button members 921, 922 (see FIG. 7). The latch pin unit 90 includes upper and lower latch pins 901, 902 which are respectively disposed on the upper and lower button members 921, 922 so as to be respectively movable with the upper and lower button members 921, 922 between the engaging and disengaging positions. The biasing unit 93 is disposed between the upper and lower latch pins 901, 902 to bias the upper and lower latch pins 901, 902 to the engaging position. The press button unit 92 is movably bonded to the cover body 91 via the biasing unit 93. The biasing unit 93 includes upper and lower biasing members 931, 932. The upper biasing member 931 is disposed between the upper button member 921 and a protrusion 912 extending inwardly from an inner surface 910 of the cover body 91 so as to bias the upper latch pin 901 on the upper button member 921 to the engaging position. The lower biasing member 932 is disposed between the lower button member 922 and the protrusion 911 so as to bias the lower latch pin 902 on the lower button member 922 to the engaging position.

In this embodiment, as best shown in FIGS. 2 and 5, the pad bracket 21 has a surrounding rim 216 and a groove 211. The surrounding rim 216 extends outwardly from the outward major surface 212 to define a concave region 217. The groove 211 is formed in and across the concave region 217.

In this embodiment, the joint orthosis further includes a positioning plate 22 and a leaf spring 23 (see FIGS. 2 and 3). The positioning plate 22 is configured to be fitted in the concave region 217 to conceal the groove 211 (see FIG. 5), and includes front and rear locating holes 222, 221. The leaf spring 23 is disposed in the groove 211, and extends along the groove 211 to terminate at front and rear clip ends 232, 231 which extend outwardly of the front and rear locating holes 222, 221, respectively. Each of the front and rear clip ends 232, 231 is configured to bias the respective protuberance 83, 83', 73 or 73' to be in full engagement in a corresponding one of the front and rear jaw cavities 63, 62.

The inner major surface 801, 801', 701, or 701' of each of the modular front and rear inserts 8, 8', 7, or 7' is formed with a positioning recess 811, 811', 711, or 711' (see FIG. 5) which is configured to be in snap engagement with a corresponding one of the front and rear clip ends 232, 231.

The shielding cover 9 further has front and rear gripping members 94, 95 (see FIG. 7), each of which is configured to grip a corresponding one of the protuberances 83, 73, 83', 73', when the shielding cover 9 is attached to the mounting frame 6. The front gripping member 94 includes two front plate portions 941 for gripping the protuberance 83 or 83'. The rear gripping member 95 includes two rear plate portions 951 for gripping the protuberance 73 or 73'.

When using the joint orthosis, a user can select a suitable one of the modular front inserts 8, 8' to limit the movement of a joint in a flexion direction, and can select a suitable one of the modular rear inserts 7, 7' to limit the movement of the joint in an extension direction. To prevent misinsertion of the modular front insert 8 or 8' into the rear contoured area 43 and to prevent misinsertion of the modular rear insert 7 or 7' into the front contoured area 44, the protuberances 83, 83' of the modular front inserts 8, 8' are different from those of the modular rear inserts 7, 7' in shape.

In this embodiment, the joint orthosis further includes inner and outer washer plates 30, 33 each being 8-shaped (see FIG. 2). The inner washer plate 30 has an inner upper half 31 disposed between the positioning plate 22 and the upper pivot segment 4, and an inner lower half 32 disposed between the positioning plate 22 and the lower pivot segment 5. The outer washer plate 33 has an outer upper half 34 disposed between the mounting frame 6 and the upper pivot segment 4, and an outer lower half 35 disposed between the mounting frame 6 and the lower pivot segment 5.

Figure 10:
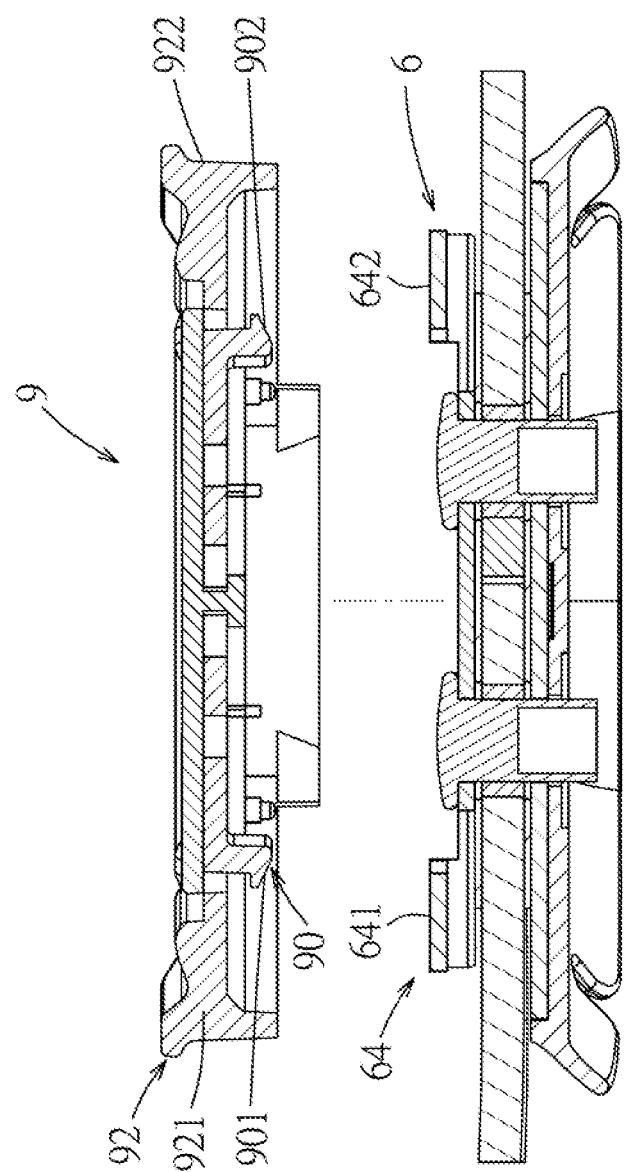
FIG. 10 is a cross-sectional view similar to FIG. 8 but illustrating that the shield cover is removed from the joint orthosis.
Figure 11:
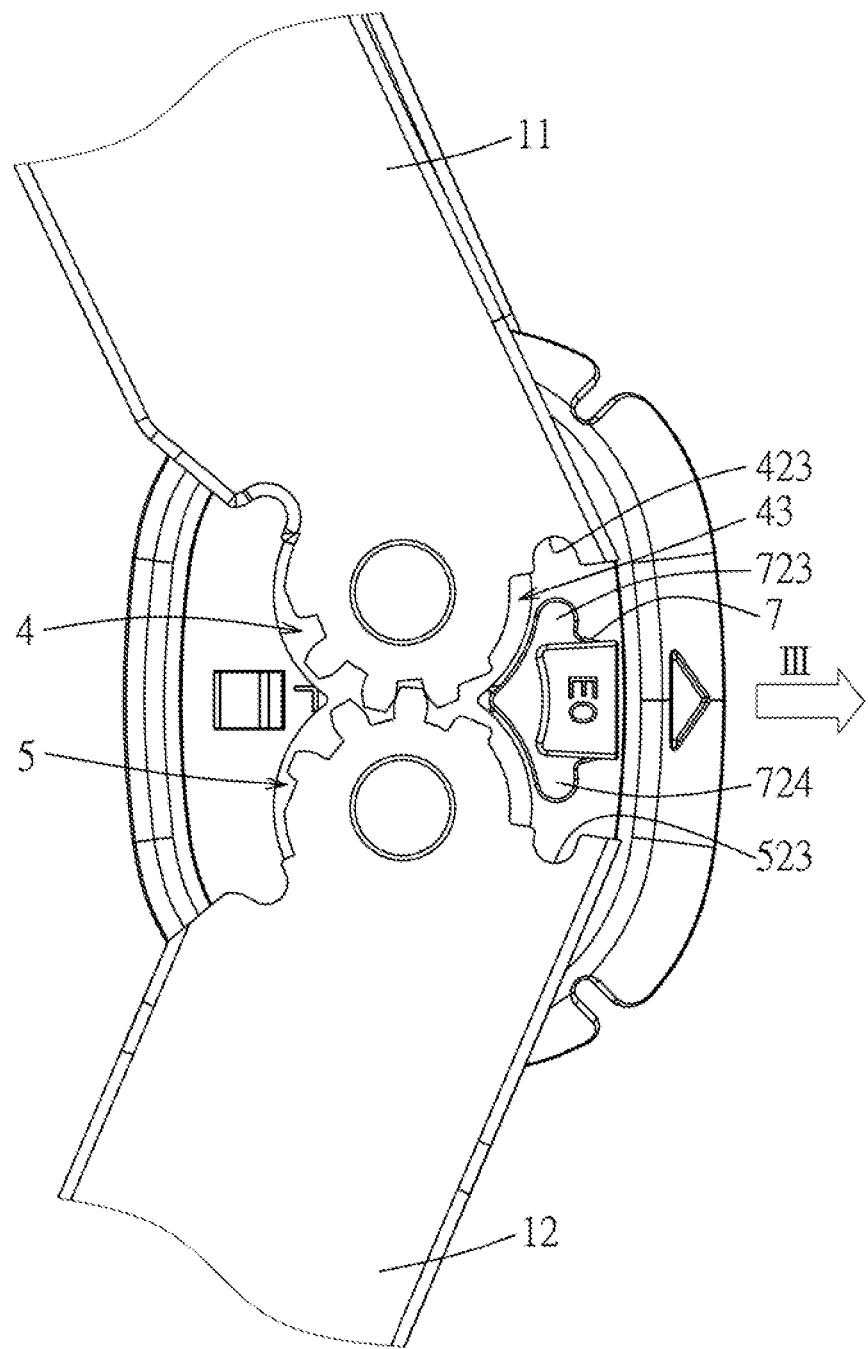
FIG. 11 is a fragmentary enlarged view similar to FIG. 6 but illustrating that a modular front insert has been removed to permit a flexion movement of the joint orthosis.

As shown in FIG. 6, the modular front and rear inserts 8, 7 are fitted in the front and rear contoured areas 44, 43, respectively. In this case, the joint of the user protected by the joint orthosis is prevented from movement, in both flexion and extension directions. To adjust flexion/extension angle limits of the joints, the user can press the upper and lower button members 921, 922 in directions (I-1), (I-2), respectively (FIG. 8) to cause the upper and lower latch pins 901, 902 to move to the disengaging position (FIG. 9). Then, the shielding cover 9 is removed (FIG. 10). The modular front insert 8 is pulled out from the front contoured area 44 via the protuberance 33 in a direction (II) (FIG. 6). The upper and lower members 11, 12 rotate about the upper and lower axes, respectively (see arrows A and B in FIG. 6), thereby permitting the rear upper and lower mortise cavities 423, 523 to respectively disengage from the upper and lower tenon ends 723, 724 (see FIG. 11). The modular rear insert 7 is pulled out from the rear contoured area 43 via the protuberance 73 in a direction (III). With reference to FIG. 12, to limit the movement of the joint in the flexion direction, the modular front insert 8' can be inserted into the front contoured area 44 in a direction (V) such that the modular front insert 8' is in snap engagement with the front clip end 232 of the leaf spring 23. To limit the movement of the joint in the extension direction, the modular rear insert 7' can be inserted into the rear contoured area 43 in a direction (IV) such that the modular rear insert 7' is in snap engagement with the rear clip end 231 of the leaf spring 23. Finally, the shielding cover 9 is attached to the mounting frame 6. It should be noted that the user may insert only one of the modular front and rear inserts 8, 8', 7, or 7' into the joint mechanism 20.

In this embodiment, each of the modular front and rear inserts 8, 8', 7, 7' can be easily pulled out from the respective joint mechanism 20. In addition, the shielding cover 9 is removably attached to the mounting frame 6 and is configured to prevent access to each of the modular front and rear inserts 8, 8', 7, 7'. Thus, each of the modular front and rear inserts 8, 8', 7, 7' disposed in the respective joint mechanism 20 can be prevented from falling out. With the provision of the shielding cover 9, the mounting frame 6, and the leaf spring 23 for concealing/positioning the modular insert 8, 8', 7, or 7', the joint orthosis of this invention is more durable than the joint orthosis disclosed in U.S. Pat. No. 7,887,496.

While the present invention has been described in connection with what is considered the most practical embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A joint orthosis comprising: upper and lower members, said upper member including an upper pivot segment which has an upper pivot bore defining an upper axis and an upper peripheral interacting region that extends angularly about the upper axis and that includes a front upper terminal area, a rear upper terminal area, and upper teeth that are displaced from each other about the upper axis and that are disposed between said front and rear upper terminal areas, said lower member including a lower pivot segment which has a lower pivot bore defining a lower axis and a lower peripheral interacting region that extends angularly about the lower axis and that includes a front lower terminal area, a rear lower terminal area, and lower teeth that are displaced from each other about the lower axis, and that are disposed between said front and rear lower terminal areas, said front upper and lower terminal areas cooperatively defining therebetween a front contoured area having a first front dimension, said rear upper and lower terminal areas cooperatively defining therebetween a rear contoured area having a first rear dimension, said upper and lower teeth interlocking with each other such that when at least one of said upper and lower members is permitted to rotate about at least a corresponding one of said upper and lower axes, said front and rear contoured areas are configured to be transformed from having the first front and rear dimensions to having second front and rear dimensions, respectively; at least one of modular front and rear inserts, said modular front and rear inserts each being configured to be fitted in a corresponding one of said front and rear contoured areas having the second front and rear dimensions, respectively, and each having an inner major surface, an outer major surface, and a protuberance extending outwardly from said outer major surface; a mounting frame disposed outwardly of said upper and lower pivot segments, and having front and rear jaw cavities each of which is configured to permit said respective protuberance to be engaged therein, said mounting frame further having upper and lower frame holes aligned with said upper and lower pivot bores, respectively; a pad bracket disposed inwardly of said upper and lower pivot segments, and having an outward major surface confronting said upper and lower pivot segments, and an inward major surface adapted to be pressed against a pad, said pad bracket further having upper and lower bracket holes aligned with said upper and lower pivot bores, respectively; an upper pivot bolt configured to pass through said upper frame hole, said upper pivot bore, and said upper bracket hole so as to permit said upper member to be pivotally mounted thereon, thereby permitting said upper member to be pivotable about the upper axis relative to said mounting frame and said pad bracket; a lower pivot bolt configured to pass through said lower frame hole, said lower pivot bore, and said lower bracket hole so as to permit said lower member to be pivotally mounted thereon, thereby permitting said lower member to be pivotable about the lower axis relative to said mounting frame and said pad bracket; and a shielding cover removably attached to said mounting frame, and configured to conceal and prevent access to said at least one of said modular front and rear inserts, wherein said mounting frame further has a retaining unit, and said shielding cover has a latch pin unit which is movable between an engaging position, where said latch pin unit is engaged with said retaining unit, and a disengaging position, where said latch pin unit is disengaged from said retaining unit, a biasing unit disposed to bias said latch pin unit to the engaging position, and a press button unit configured to be manually pressed against a biasing action of said biasing unit to move said latch pin unit to the disengaging position.

2. The joint orthosis according to claim 1, wherein each of said modular front and rear inserts further has a minor surface including upper and lower gliding regions which extend respectively away from said respective protuberance so as to permit said upper and lower teeth to freely glide thereon.

3. The joint orthosis according to claim 2, wherein said upper and lower gliding regions of said minor surface of each of said modular front and rear inserts extend to respectively terminate at upper and lower tenon ends,
said front upper terminal area being formed with a front upper mortise cavity, said rear upper terminal area being formed with a rear upper mortise cavity, said front lower terminal area being formed with a front lower mortise cavity, said rear lower terminal area being formed with a rear lower mortise cavity, said upper tenon end being fitted in a corresponding one of said front and rear upper mortise cavities and said lower tenon end being fitted in a corresponding one of said front and rear lower mortise cavities when said front and rear contoured areas have the second front and rear dimensions, respectively.

4. The joint orthosis according to claim 3, wherein said upper peripheral interacting region further includes an upper toothless area disposed between said rear upper terminal area and said upper teeth, and
said lower peripheral interacting region further includes a lower toothless area disposed between said rear lower terminal area and said lower teeth.

5. The joint orthosis according to claim 1, wherein said retaining unit includes upper and lower retaining members, and said press button unit includes upper and lower button members, said latch pin unit including upper and lower latch pins which are disposed to be respectively movable with said upper and lower button members between the engaging and disengaging positions, wherein said biasing unit is disposed between said upper and lower latch pins to bias said upper and lower latch pins to the engaging position.

6. The joint orthosis according to claim 1, comprising a pair of said modular front inserts and a pair of said modular rear inserts, each of said front pair and said rear pair of said modular inserts being configured to have different dimensions so as to respectively match said first and second dimensions of a corresponding one of said front and rear contoured areas.

7. The joint orthosis according to claim 1, wherein said shielding cover has front and rear gripping members each of which is configured to grip said respective protuberance when said shielding cover is attached to said mounting frame.

8. A joint orthosis comprising: upper and lower members, said upper member including an upper pivot segment which has an upper pivot bore defining an upper axis and an upper peripheral interacting region that extends angularly about the upper axis and that includes a front upper terminal area, a rear upper terminal area, and upper teeth that are displaced from each other about the upper axis and that are disposed between said front and rear upper terminal areas, said lower member including a lower pivot segment which has a lower pivot bore defining a lower axis and a lower peripheral interacting region that extends angularly about the lower axis and that includes a front lower terminal area, a rear lower terminal area, and lower teeth that are displaced from each other about the lower axis, and that are disposed between said front and rear lower terminal areas, said front upper and lower terminal areas cooperatively defining therebetween a front contoured area having a first front dimension, said rear upper and lower terminal areas cooperatively defining therebetween a rear contoured area having a first rear dimension, said upper and lower teeth interlocking with each other such that when at least one of said upper and lower members is permitted to rotate about at least a corresponding one of said upper and lower axes, said front and rear contoured areas are configured to be transformed from having the first front and rear dimensions to having second front and rear dimensions, respectively; at least one of modular front and rear inserts, said modular front and rear inserts each being configured to be fitted in a corresponding one of said front and rear contoured areas having the second front and rear dimensions, respectively, and each having an inner major surface, an outer major surface, and a protuberance extending outwardly from said outer major surface; a mounting frame disposed outwardly of said upper and lower pivot segments, and having front and rear jaw cavities each of which is configured to permit said respective protuberance to be engaged therein, said mounting frame further having upper and lower frame holes aligned with said upper and lower pivot bores, respectively; a pad bracket disposed inwardly of said upper and lower pivot segments, and having an outward major surface confronting said upper and lower pivot segments, and an inward major surface adapted to be pressed against a pad, said pad bracket further having upper and lower bracket holes aligned with said upper and lower pivot bores, respectively; an upper pivot bolt configured to pass through said upper frame hole, said upper pivot bore, and said upper bracket hole so as to permit said upper member to be pivotally mounted thereon, thereby permitting said upper member to be pivotable about the upper axis relative to said mounting frame and said pad bracket; a lower pivot bolt configured to pass through said lower frame hole, said lower pivot bore, and said lower bracket hole so as to permit said lower member to be pivotally mounted thereon, thereby permitting said lower member to be pivotable about the lower axis relative to said mounting frame and said pad bracket; and a shielding cover removably attached to said mounting frame, and configured to conceal and prevent access to said at least one of said modular front and rear inserts, wherein said pad bracket has a surrounding rim extending outwardly from said outward major surface to define a concave region, and a groove formed in and across said concave region, said joint orthosis further comprising a positioning plate configured to be fitted in said concave region to conceal said groove, and having front and rear locating holes, and a leaf spring disposed in said groove, and extending along said groove to terminate at front and rear clip ends which extend outwardly of said front and rear locating holes, respectively, and each of which is configured to bias said, respective protuberance to be in full engagement in a corresponding one of said front and rear jaw cavities.

9. The joint orthosis according to claim 8, wherein said inner major surface of each of said modular front and rear inserts is formed with a positioning recess which is configured to be in snap engagement with a corresponding one of said front and rear clip ends.

10. The joint orthosis according to claim 8, further comprising
an inner washer plate having an inner upper half disposed between said positioning plate and said upper pivot segment, and an inner lower half disposed between said positioning plate and said lower pivot segment, and
an outer washer plate having an outer upper half disposed between said mounting frame and said upper pivot segment, and an outer lower half disposed between said mounting frame and said lower pivot segment.

* * * * *